United States Patent [19]
LeGrow et al.

[11] Patent Number: 5,274,156
[45] Date of Patent: Dec. 28, 1993

[54] ORGANOSILOXANE ETHERS

[75] Inventors: Gary E. LeGrow; Milan F. Sojka, both of Midland, Mich.

[73] Assignee: Dow Corning Corporation, Midland, Mich.

[21] Appl. No.: 57,923

[22] Filed: May 7, 1993

[51] Int. Cl.$^5$ ............................................. C07F 7/08
[52] U.S. Cl. ........................................ 556/445; 528/25; 528/29; 424/78.03
[58] Field of Search .............. 556/445; 528/25, 29; 514/63; 424/78.03

[56] References Cited

U.S. PATENT DOCUMENTS

| | | | |
|---|---|---|---|
| 2,846,458 | 8/1958 | Haluska | 260/448.2 |
| 4,736,049 | 4/1988 | Suzuki et al. | 556/445 X |
| 4,847,398 | 7/1989 | Mehta et al. | 556/445 |
| 5,057,549 | 10/1991 | Herzig et al. | 528/25 X |
| 5,068,382 | 11/1991 | Rauleder et al. | 556/445 |
| 5,110,970 | 5/1992 | Blevins et al. | 556/445 |
| 5,118,772 | 6/1992 | Herzig et al. | 556/445 X |
| 5,144,054 | 9/1992 | Shioya et al. | 556/445 |

Primary Examiner—Paul F. Shaver
Attorney, Agent, or Firm—James L. DeCesare

[57] ABSTRACT

A method is described of producing a mixture of silicone polyethers from a mixture of at least two alkenyl ether terminated organic oxyalkylene compounds having different molecular weights and an organosilicon compound having at least two hydride substituents. In an alternate embodiment, an organocyclosilazane is used, and either alkyl or alkenyl ether terminated organic oxyalkylene compounds can be employed. The mixtures have utility in the conditioning of skin.

20 Claims, No Drawings

ORGANOSILOXANE ETHERS

BACKGROUND OF THE INVENTION

This invention is directed to organosiloxane ethers, and to methods of making organosiloxane ethers. In particular, a unique mixture of organosiloxane ethers is provided, and two methods of making these organosiloxane ether mixtures are disclosed.

Organosiloxane ethers are known in the art. For example, in U.S. Pat. No. 2,846,458 issued Aug. 5, 1958, there is described a process of preparing organosiloxane ethers in which an unsaturated ether is reacted with a siloxane containing the ≡-SiH group. In the method described in the '458 patent, one unsaturated ether compound is reacted with one siloxane compound containing the ≡-SiH group, and one organosiloxane ether product is produced.

It has been unexpectedly discovered that if such a reaction is conducted between at least two unsaturated ethers, with one siloxane compound containing at least two ≡-SiH groups, that a mixture of three distinct organosiloxane ethers can be obtained. The feature which is unexpected is the fact that the mixture of the three distinct organosiloxane ethers produced in accordance with the present invention, has been found to contain a third organosiloxane ether which cannot be produced by reacting either of the unsaturated ethers individually with the siloxane containing the ≡-SiH groups.

In an alternate embodiment of the invention, the same result has been achieved by reacting at least two ethers with an organocyclosilazane.

SUMMARY OF THE INVENTION

The invention relates to a mixture of silicone polyethers prepared by a method in which at least two alkenyl ether terminated oxyalkylene compounds are reacted with a silicone hydride, to produce a mixture containing at least three silicone polyethers having different molecular weights.

The invention also relates to a mixture of silicone polyethers prepared by an alternate route in which at least two alkyl or alkenyl ether terminated oxyalkylene compounds are reacted with an organocyclosilazane, to produce a mixture containing at least three silicone polyethers having different molecular weights.

The mixtures of silicone polyethers produced in accordance with either method have been found to possess utility as a conditioning agent for personal care compositions for application to human skin.

These and other objects, features, and advantages, of the herein described present invention will become more apparent from a consideration of the following detailed description thereof.

DETAILED DESCRIPTION OF THE INVENTION

The uniqueness of the present invention can best be described by considering a scenario in which a silicone hydride such as $HMe_2SiOSiMe_2H$ is reacted with an alkenyl ether terminated organic oxyalkylene compound such as $H_2C=CH-CH_2-O-(CH_2-CH_2O)_{12}-H$. If the silicone hydride is considered unit "B" and the oxyalkylene compound as unit "A", then the reaction will produce copolymers containing the units "ABA" with about 20-28 total of the "A" units. If the same silicone hydride $HMe_2SiOSiMe_2H$ identified as "B" is reacted with a different alkenyl ether terminated organic oxyalkylene compound considered as unit "C" such as $H_2C=CH-CH_2-O-(CH-CH_2O)_{20}-H$, the reaction will produce copolymers containing the units "CBC" with a total of about 36-44 of the "C" units.

What has been discovered in accordance with the present invention, is that by simultaneously reacting the silicone hydride $HMe_2SiOSiMe_2H$ identified as "B", with both of the organic oxyalkylene compounds $H_2C=CH-CH_2-O-(CH-CH_2O)_{12}-H$ identified as "A" and $H_2C=CH-CH_2-O-(CH_2-CH_2O)_{20}-H$ identified as "C", there is produced a mixture containing not only copolymers "ABA" containing 20-28 "A" units and copolymers "CBC" containing 36-44 "C" units, but in addition there is produced and there is present in the reaction mixture the copolymer "ABC" containing 28-36 "A" and "C" units. The copolymer "ABC" cannot be obtained by the methods of the prior art as exemplified by the '458 patent discussed above.

In one embodiment according to the present invention, there is provided a method of producing a mixture of silicone polyethers by the steps of: (i) preparing a mixture of at least two alkenyl ether terminated organic oxyalkylene compounds having different molecular weights; (ii) adding to the mixture of alkenyl ether terminated organic oxyalkylene compounds, an organosilicon compound having at least two hydride substituents; (iii) while heating, contacting the mixture of the two oxyalkylene compounds and the organosilicon compound with a catalytically effective amount of a noble metal catalyst, under conditions to react the alkenyl ether substituent of the oxyalkylene compounds with the hydride substituents of the organosilicon compound; and (iv) separating from the reaction mixture a product which is mixture of at least three silicone polyethers having different molecular weights.

The organosilicon compound is a silicone hydride, and the oxyalkylene compounds each may contain in the molecule oxyethylene groups, oxypropylene groups, or both oxyethylene groups and oxypropylene groups.

Examples of some organosilicon hydrides which can be employed are compounds such as $HMe_2SiOSiMe_2H$; $HMe_2SiO(Me_2SiO)_nSiMe_2H$ in which n has a value of one to two hundred; $(HMeSiO)_x$ in which x has a value of four to six; $(HMeSiO)_a(Me_2SiO)_b$ in which a and b are each equal to or greater than two; $Me_3SiO(MeHSiO)_xSiMe_3$ in which x has a value equal to or greater than two; and $Me_3SiO(MeHSiO)_x(Me_2SiO)_ySiMe_3$ in which x has a value equal to or greater than two and y has a value equal to or greater is than one. In these formulas, Me is methyl.

Suitable alkenyl ether terminated organic oxyalkylene compounds which can be employed should contain at least three to about ten carbon atoms in the alkenyl group, and some examples of groups which can be used are allyl, isopropenyl, 2-butenyl, 3-butenyl, or hexenyl. Allyl is the most preferred alkenyl group and some allyl ether terminated organic oxyalkylene compounds which may be employed are:

$H_2C=CH-CH_2-O-(CH_2CH_2O)_m-H$;
$H_2C=CH-CH_2-O-(CH_2-CH_2O)_n-H$;
$H_2C=CH-CH_2-O-[CH_2-CH(CH_3)O]_m-H$;
$H_2C=CH-CH_2-O-[CH_2-CH(CH_3)O]_n-H$;
$H_2C=CH-CH_2-O-(CH_2-CH_2O)_m-[CH_2CH(CH_3)O]_m-H$;

$H_2C=CH-CH_2-O-(CH_2-CH_2O)_n-[CH_2-CH(CH_3)O]_n-H$;

$H_2C=CH-CH_2-O-(CH_2-CH_2O)_m-[CH_2-CH(CH_3)O]_n-H$; and $H_2C=CH-CH_2-O-(CH_2-CH_2O)_n-[CH_2-CH(CH_3)O]_m-H$; in which m has a value of 10-14 and n has a value of 18-22.

In this method, it is preferred to conduct the hydrosilylation reaction with an allyl to SiH ratio of 1.0 to 1.1.

The composition of a typical reaction product is obtained from the above method of the present invention includes a mixture of silicone polyether compounds having the formulas:

$H-(OCH_2-CH_2)_m-O(CH_2)_3SiMe_2OMe_2Si(CH_2)_3O-(CH_2-CH_2O)_m-H$;

$H-(OCH_2-CH_2)_m-O(CH_2)_3SiMe_2OMe_2Si(CH_2)_3O-(CH_2-CH_2O)_n-H$; and $H-(OCH_2-CH_2)_n-O(CH_2)_3SiMe_2OMe_2Si(CH_2)_3O-(CH_2-CH_2O)_n-H$; in which Me is methyl, m has a value of 10-14, and n has a value of 18-22. Most preferably, m is twelve and n is twenty.

In an alternate embodiment of the present invention, there is provided a method of producing a mixture of organosilicon polyethers by the steps of: (i) preparing a mixture of at least two alkenyl or alkyl ether terminated organic oxyalkylene compounds having different molecular weights, the oxyalkylene compounds each having in the molecule oxyethylene groups, oxypropylene groups, or both oxyethylene groups and oxypropylene groups; (ii) adding to the mixture of alkenyl ether terminated organic oxyalkylene compounds an organosilicon compound which is an organocyclosilazane having the formula $[R(CH_3)SiNH]_z$ in which R is an aliphatic hydrocarbon radical having from one to twenty carbon atoms and z has a value of three to six; (iii) while heating, contacting the mixture of the two oxyalkylene compounds and the organosilicon compound under conditions to react the alkenyl ether terminated organic oxyalkylene compounds with the organosilicon compound; (iv) separating ammonia from the reaction mixture by heating the mixture; and (v) recovering a product which is mixture of at least three organosilicon polyethers having different molecular weights.

Suitable organocyclosilazane compounds which can be employed in this embodiment of the invention are compounds such as $(Me_2SiNH)_3$; $(Me_2SiNH)_4$; $(EtMeSiNH)_5$; $(ViMeSiNH)_5$; $[C_3H_5(Me)SiNH]_4$; $[Me_2CH(Me)SiNH]_3$; and $[(C_{18}H_{37})MeSiNH]_3$. In these formulas, Me is methyl, Et is ethyl, and Vi is vinyl.

In this embodiment, it is preferred to conduct the silylation reaction with a polyol to silazane ratio of 1.0 to 1.1. The same alkenyl ether terminated organic oxyalkylene compounds noted above are again employed. However, a different type of product is separated from the reaction mixture. The product includes organosilicon polyether compounds having the formulas:

$CH_2=CH-CH_2-(OCH_2CH_2)_m-O-SiMeR-O-(CH_2CH_2O)_m-CH_2-CH=CH_2$;

$CH_2=CH-CH_2-(OCH_2CH_2)_n-O-SiMeR-O-(CH_2CH_2O)_n-CH_2-CH=CH_2$; and $CH_2=CH-CH_2-(OCH_2CH_2)_m-O-SiMeR-O-(CH_2CH_2O)_n-CH_2-CH=CH_2$. In these formulas, Me is methyl, m has a value of 10-14, and n has a value of 18-22. Again, most preferably m is twelve and n is twenty.

Where the oxyalkylene compounds are alkyl terminated, instead of alkenyl terminated, it is preferred to use compounds having from one to about ten carbon atoms in the alkyl group. Examples of some compounds which may be employed are:

$CH_3-O-(CH_2-CH_2O)_m-H$;

$CH_3-O-(CH_2-CH_2O)_n-H$;

$CH_3-O-[CH_2-CH(CH_3)O]_m-H$;

$CH_3-O-[CH_2-CH(CH_3)O]_n-H$;

$CH_3-O-(CH_2-CH_2O)_m-[CH_2-CH(CH_3)O]_m-H$;

$CH_3-O-(CH_2-CH_2O)_n-[CH_2-CH(CH_3)O]_n-H$;

$CH_3-O-(CH_2-CH_2O)_m-[CH_2-CH(CH_3)O]_n-H$; and $CH_3-O-(CH_2-CH_2O)_n-[CH_2-CH(CH_3)O]_m-H$; in which m has a value of 10-14 and n has a value of 18-22.

It is preferred to conduct the silylation reaction with a polyol to silazane ratio of 1.0 to 1.1. The product separated from the reaction mixture of this third embodiment of the invention, and wherein the alkyl group of the is oxyalkylene compound selected is methyl, include organosilicon polyether compounds having the formulas:

$CH_3-(OCH_2CH_2)_m-O-SiMe_2-O-(CH_2CH_2O)_m-CH_3$;

$CH_3-(OCH_2CH_2)_n-O-SiMe_2-O-(CH_2CH_2O)_n-CH_3$; and $CH_3-(OCH_2CH_2)_m-O-SiMe_2-O-(CH_2CH_2O)_n-CH_3$; in which m has a value of 10-14, and n has a value of 18-22.

Any of the above mixtures of products can be used in the conditioning of human skin by applying to the skin an effective amount the mixture containing at least three of the silicone polyethers.

The products of the hydrosilylation reaction are best made by reacting the allyl ether of the desired oxyalkylene compound with the corresponding siloxane containing SiH groups. This reaction is best carried out by heating a mixture of the three reactants in the presence of a platinum catalyst such as platinum dispersed on an inert carrier or a compound of platinum such as chloroplatinic acid, at temperatures from 30°-100° C. The hydrosilylation reaction can be depicted as follows:

$HMe_2SiOSiMe_2H + H_2C=CH-CH_2-O-(CH_2-CH_2O)_m-H + H_2C=CH-CH_2-O-(CH_2-CH_2O)_n-H \rightarrow$ 25% $H-(OCH_2-CH_2)_m-O(CH_2)_3SiMe_2OMe_2Si(CH_2)_3O-(CH_2-CH_2O)_m-H$ 50% $H-(OCH_2-CH_2)_m-O(CH_2)_3SiMe_2OMe_2Si(CH_2)_3O-(CH_2-CH_2O)_n-H$ 25% $H-(OCH_2-CH_2)_n-O(CH_2)_3SiMe_2OMe_2Si(CH_2)_3O-(CH_2-CH_2O)_n-H$ The noble metal catalyst may be selected from a variety of hydrosilation catalysts known to promote the reaction of vinyl-functional radicals with silicon-bonded hydrogen atoms. Suitable noble metal catalysts include platinum and rhodium-containing compounds and complexes. Platinum catalysts such as platinum acetylacetonate or chloroplatinic acid are representative of these compounds and suitable for use. A preferred catalyst mixture is a chloroplatinic acid complex of divinyltetramethyldisiloxane diluted in dimethylvinylsiloxy endblocked polydimethylsiloxane which may be prepared according to methods described by Willing in U.S. Pat. No. 3,419,593. Most preferably this mixture contains about 0.6 weight percent platinum.

Hydrosilation catalysts are well known in the art and the interested reader is referred to the following patents for detailed descriptions regarding their preparation and use: Speier, U.S. Pat. No. 2,823,218; Willing, U.S. Pat. No. 3,419,359; Kookootsedes, U.S. Pat. No. 3,445,420; Polmanteer et al, U.S. Pat. No. 3,697,473; Nitzsche, U.S. Pat. No. 3,814,731; Chandra, U.S. Pat. No. 3,890,359; and Sandford, U.S. Pat. No. 4,123,604. Many of the catalysts known in the art require the reactants to be heated in order for reaction to occur. When such catalysts are employed, this requirement must be taken into consideration.

When platinum catalysts are used, an inhibitor may be required in order to improve the shelf life of the starting materials and to control the viscosity-time profile of the compositions. These inhibitors are also known in the art and include ethylenically unsaturated isocyanurates, such as trialkylisocynurate, dialkylacetylenedicarboxylates, alkyl maleates, phosphines, phosphites, aminoalkyl silanes, sulphoxides, acrylonitrile derivatives and others. Particular inhibitors preferably used are diethyl fumarate, bis (2-methoxy-1-methylene) maleate, bis (2-methoxy-1-methylethyl) maleate, and similar compounds.

The concentrations of the catalyst and inhibitor to be used in the present invention may be determined by routine experimentation. Typically, however, the effective amount of catalyst should be in a range so as to provide from about 0.1 to 1,000 parts per million (ppm) of platinum by weight in the compositions of the present invention. A ratio by weight of inhibitor to catalyst mixture ranging from zero to about 0.6 provides a suitable wide range of inhibition which is adequate under most practical conditions of manufacture. Cosmetic use of the compositions requires purification of the product to remove traces of catalyst and inhibitor, however.

The alternate silylation reaction used to make products in accordance with the present invention can be depicted as follows:

$(Me_2SiNH)_3 + H_2C=CH-CH_2-O-(CH_2CH_2O)_m-H + H_2C=CH-CH_2-O-(CH_2-CH_2O)_n-H \rightarrow$ (I) $CH_2=CH-CH_2-(OCH_2CH_2)_m-O-SiMe_2-O-(CH_2CH_2O)_m-CH_2-CH=CH_2$ (II) $CH_2=CH-CH_2-(OCH_2CH_2)_n-O-SiMe_2-O-(CH_2CH_2O)_n-CH_2-CH=CH_2$ (III) $CH_2=CH-CH_2-(OCH_2CH_2)_m-O-SiMe_2-O-(CH_2CH_2O)_n-CH_2-CH=CH_2$ A one to one molar mixture of the two allyl ethers in accordance with this embodiment provides a mixture of the three products I, II, and III, in a ratio of 1:1:2.

The following examples are set forth for the purpose of illustrating the concepts embodied in the present invention in more detail.

EXAMPLE I

To a mixture of 615 g. (1.05 mole) of allyl-O-$(CH_2CH_2O)_{12}$-H and 985 g. (1.05 mole) of allyl-O-$(CH_2CH_2O)_{20}$-H was added 0.01 g. of chloroplatinic acid in isopropyl alcohol. The mixture was heated to 80° C. With stirring, 134 g. (1.0 mole) of $(HMe_2Si)_2O$ was slowly added over a period of 1 hour. Addition of a small sample of this mixture to a >pH=12 solution of NaOH in water showed no gas evolution, and thus no unreacted Si-H content. The product was allowed to cool to room temperature forming a waxy solid with a softening point of approximately 27° C. The chemical composition of the product is as follows:

25% H-$(OCH_2$-$CH_2)_{12}$-$O(CH_2)_3SiMe_2OMe_2Si(CH_2$-$)_3O$-$(CH_2$-$CH_2O)$ $_{12}$-H

50% H-$(OCH_2$-$CH_2)_{12}$-$O(CH_2)_3SiMe_2OMe_2Si(CH_2$-$)_3O$-$(CH_2$-$CH_2O)$ $_{20}$-H

25% H-$(OCH_2$-$CH_2)_{20}$-$O(CH_2)_3SiMe_2OMe_2Si(CH_2$-$)_3O$-$(CH_2$-$CH_2O)$ $_{20}$-H

Gel Permeation Chromatographic (GPC) analysis of this mixture showed a broad curve verifying that it had an average molecular weight of approximately 1650, and a range of molecular weight from 1300 to 2100.

EXAMPLE II

Addition of $(HMe_2Si)_2O$ to the two polyethers used above in Example I separately, followed by equimolar mixing of the products produce a material of the following composition:

50% H-$(OCH_2$-$CH_2)_{12}$-$O(CH_2)_3SiMe_2OMe_2Si(CH_2$-$)_3O$-$(CH_2$-$CH_2O)$ $_{12}$-H

50% H-$(OCH_2$-$CH_2)_{20}$-$O(CH_2)_3SiMe_2OMe_2Si(CH_2$-$)_3O$-$(CH_2$-$CH_2O)$ $_{20}$-H

The component which is absent but which was produced in accordance with the method of Example I is: H-$(OCH_2$-$CH_2)_{12}$-$O(CH_2)_3SiMe_2$ $OMe_2Si(CH_2)_3O$-$(CH_2$-$CH_2O)_{20}$-H GPC analysis of the product of Example II showed a bimodal curve corresponding to molecular weights of 1300 and 2100. The peak at 1650, present in Example I was absent in Example II.

EXAMPLE III

A catalyst of 0.075 g of phosphoric acid ($H_3PO_4$ 99%) was added to a mixture of 293.5 g of methyl -O-$(CH_2$-$CH_2$-$O)_{20}$-H and 183.5 g of methyl-O-$(CH_2$-$CH_2$-$O)_{12}$- H at 60° C. Under stirring at 100 rpm, 23 g of hexamethylcyclotrisilazane was added. After the elapse of one hour, the system was heated up to 65° C. for an additional 17 hours. A slow stream of nitrogen and vacuum of 90 mm Mg was kept during the entire time to remove ammonia. The phosphoric acid in the ammonia free product was neutralized by 0.18 g of sodium bicarbonate. The system was allowed to coal to room temperature. A waxy solid formed with a softening point of approximately 30° C.

Other variations and modifications may be made in the compounds, compositions, and methods, described herein without departing from the essential features and concepts of the present invention. The forms of the invention described herein are exemplary only and are not intended as limitations on the scope of the invention as defined in the appended claims.

That which is claimed is:

1. A method of producing a mixture of silicone polyethers comprising the steps of: (i) preparing a mixture of at least two alkenyl ether terminated organic oxyalkylene compounds having different molecular weights; (ii) adding to the mixture of alkenyl ether terminated organic oxyalkylene compounds, an organosilicon compound having at least two hydride substituents; (iii) while heating, contacting the mixture of the two oxyalkylene compounds and the organosilicon compound with a catalytically effective amount of a noble metal catalyst, under conditions to react the alkenyl ether substituent of the oxyalkylene compounds with the hydride substituents of the organosilicon compound; and (iv) separating from the reaction mixture a product which is mixture of at least three silicone polyethers having different molecular weights.

2. A method according to claim 1 in which the organosilicon compound is a silicone hydride; and the oxyalkylene compounds each contain in the molecule oxyethylene groups, oxypropylene groups, or both oxyethylene groups and oxypropylene groups.

3. A method according to claim 2 in which the organosilicon hydride is a compound having a formula selected from the group consisting of $HMe_2Si$-$OSiMe_2H$; $HMe_2SiO(Me_2SiO)_nSiMe_2H$ in which n has a value of one to two hundred; $(HMeSiO)_x$ in which x has a value of four to six; $(HMeSiO)_a(Me_2SiO)_b$ in which a and b are each equal to or greater than two; Me$_3$SiO(MeHSiO)$_x$SiMe$_3$ in which x has a value equal to or greater than two; and Me$_3$SiO(MeHSiO)$_x$(Me$_2$SiO)$_y$SiMe$_3$ in which x has a value equal to or greater than two and y has a value equal to or greater than one; and in which Me is methyl.

4. A method according to claim 3 in which the alkenyl ether terminated organic oxyalkylene compound is an allyl ether terminated organic oxyalkylene compound having a formula selected from the group consisting of H$_2$C=CH-CH$_2$-O-(CH$_2$-CH$_2$O)$_m$-H;
H$_2$C=CH-CH$_2$-O-(CH$_2$-CH$_2$O)$_n$-H;
H$_2$C=CH-CH$_2$-O-[CH$_2$-CH(CH$_3$)O]$_m$-H;
H$_2$C=CH-CH$_2$-O-[CH$_2$-CH(CH$_3$)O]$_n$-H;
H$_2$C=CH-CH$_2$-O-(CH$_2$-CH$_2$O)$_m$-[CH$_2$-CH(CH$_3$)O]$_m$-H;
H$_2$C=CH-CH$_2$-O-(CH$_2$-CH$_2$O)$_n$-[CH$_2$-CH(CH$_3$)O]$_n$-H;
H$_2$C=CH-CH$_2$-O-(CH$_2$-CH$_2$O)$_m$-[CH$_2$-CH(CH$_3$)O]$_n$-H; and
H$_2$C=CH-CH$_2$-O-(CH$_2$-CH$_2$O)$_n$-[CH$_2$-CH(CH$_3$)O]$_m$-H; in which m has a value of 10-14 and n has a value of 18-22.

5. A method according to claim 4 in which the product separated from the reaction mixture includes silicone polyether compounds having the formulas H-(OCH$_2$-CH$_2$)$_m$-O(CH$_2$)$_3$SiMe$_2$OMe$_2$Si(CH$_2$)$_3$O-(CH$_2$-CH$_2$O)$_m$-H;
H-(OCH$_2$-CH$_2$)$_m$-O(CH$_2$)$_3$SiMe$_2$OMe$_2$Si(CH$_2$)$_3$O-(CH$_2$-CH$_2$O)$_n$-H; and
H-(OCH$_2$-CH$_2$)$_n$-O(CH$_2$)$_3$SiMe$_2$OMe$_2$Si(CH$_2$)$_3$O-(CH$_2$-CH$_2$O)$_n$-H; in which Me is methyl, m has a value of 10-14, and n has a value of 18-22.

6. A method according to claim 5 in which m is twelve and n is twenty.

7. A method of producing a mixture of organosilicon polyethers comprising the steps of: (i) preparing a mixture of at least two alkenyl ether terminated organic oxyalkylene compounds having different molecular weights, the oxyalkylene compounds each having in the molecule oxyethylene groups, oxypropylene groups, or both oxyethylene groups and oxypropylene groups; (ii) adding to the mixture of alkenyl ether terminated organic oxyalkylene compounds, an organosilicon compound which is an organocyclosilazane having the formula [R(CH$_3$)SiNH]$_z$ in which R is an aliphatic hydrocarbon radical having from one to twenty carbon atoms and z has a value of three to six; (iii) while heating, contacting the mixture of the two oxyalkylene compounds and the organosilicon compound under conditions to react the alkenyl ether terminated organic oxyalkylene compounds with the organosilicon compound; (iv) separating ammonia from the reaction mixture by heating the mixture; and (v) recovering a product which is mixture of at least three organosilicon polyethers having different molecular weights.

8. A method according to claim 7 in which the organocyclosilazane is a compound having a formula selected from the group consisting of (Me$_2$SiNH)$_3$; (Me$_2$SiNH)$_4$; (EtMeSiNH)$_5$; (ViMeSiNH)$_5$; [C$_3$H$_5$(Me)SiNH]$_4$; [Me$_2$CH(Me)SiNH]$_3$; and [(C$_{18}$H$_{37}$)MeSiNH]$_3$; in which Me is methyl, Et is ethyl, and Vi is vinyl.

9. A method according to claim 8 in which the alkenyl ether terminated organic oxyalkylene compound is an allyl ether terminated organic oxyalkylene compound having a formula selected from the group consisting of H$_2$C=CH-CH$_2$-O-(CH$_2$-CH$_2$O)$_m$-H;
H$_2$C=CH-CH$_2$-O-(CH$_2$-CH$_2$O)$_n$-H;
H$_2$C=CH-CH$_2$-O-[CH$_2$-CH(CH$_3$0O]$_m$-H;
H$_2$C=CH-CH$_2$-O-[CH$_2$-CH(CH$_3$)O]$_n$-H;
H$_2$C=CH-CH$_2$-O-(CH$_2$-CH$_2$O)$_m$-[CH$_2$-CH(CH$_3$)O]$_m$-H;
H$_2$C=CH-CH$_2$-O-(CH$_2$-CH$_2$O)$_n$-[CH$_2$-CH(CH$_3$)O]$_n$-H;
H$_2$C=CH-CH$_2$-O-(CH$_2$-CH$_2$O)$_m$-[CH$_2$-CH(CH$_3$)O]$_n$-H; and
H$_2$C=CH-CH$_2$-O-(CH$_2$-CH$_2$O)$_n$-[CH$_2$-CH(CH$_3$)O]$_m$-H; in which m has a value of 10-14 and n has a value of 18-22.

10. A method according to claim 9 in which the product separated from the reaction mixture includes organosilicon polyether compounds having the formulas CH$_2$=CH-CH$_2$-(OCH$_2$CH$_2$)$_m$-O-SiMeR-O-(CH$_2$CH$_2$O)$_m$-CH$_2$-CH=CH$_2$;
CH$_2$=CH-CH$_2$-(OCH$_2$CH$_2$)$_n$-O-SiMeR-O-(CH$_2$CH$_2$O)$_n$-CH$_2$-CH=CH$_2$; and
CH$_2$=CH-CH$_2$-(OCH$_2$CH$_2$)$_m$-O-SiMeR-O-(CH$_2$CH$_2$O)$_n$-CH$_2$-CH=CH$_2$; in which Me is methyls m has a value of 10-14, and n has a value of 18-22.

11. A method according to claim 10 in which m is twelve and n is twenty.

12. A method of producing a mixture of organosilicon polyethers comprising the steps of: (i) preparing a mixture of at least two alkyl ether terminated organic oxyalkylene compounds having different molecular weights, the oxyalkylene compounds each having in the molecule oxyethylene groups, oxypropylene groups, or both oxyethylene groups and oxypropylene groups; (ii) adding to the mixture of alkyl ether terminated organic oxyalkylene compounds, an organosilicon compound which is an organocyclosilazane having the formula [R(CH$_3$)SiNH]$_z$ in which R is an aliphatic hydrocarbon radical having from one to twenty carbon atoms and z has a value of three to six; (iii) while heating, contacting the mixture of the two oxyalkylene compounds and the organosilicon compound under conditions to react the alkyl ether terminated organic oxyalkylene compounds with the organosilicon compound; (iv) separating ammonia from the reaction mixture by heating the mixture; and (v) recovering a product which is mixture of at least three organosilicon polyethers having different molecular weights.

13. A method according to claim 12 in which the organocyclosilazane is a compound having a formula selected from the group consisting of (Me$_2$SiNH)$_3$; (Me$_2$SiNH)$_4$; (EtMeSiNH)$_5$; (ViMeSiNH)$_5$; [C$_3$H$_5$(Me)SiNH]$_4$; [Me$_2$CH(Me)SiNH]$_3$; and [(C$_{18}$H$_{37}$)MeSiNH]$_3$; in which Me is methyls Et is ethyl, and Vi is vinyl.

14. A method according to claim 13 in which the alkyl ether terminated organic oxyalkylene compound is a methyl ether terminated organic oxyalkylene compound having a formula selected from the group consisting of CH$_3$-O-(CH$_2$-CH$_2$O)$_m$-H;
CH$_3$-O-(CH$_2$-CH$_2$O)$_n$-H;
CH$_3$-O-[CH$_2$-CH(CH$_3$)O]$_m$-H;
CH$_3$-O-[CH$_2$-CH(CH$_3$)O]$_n$-H;
CH$_3$-O-(CH$_2$-CH$_2$O)$_m$-[CH$_2$CH(CH$_3$)O]$_m$-H;
CH$_3$-O-(CH$_2$-CH$_2$O)$_n$-[CH$_2$-CH(CH$_3$O]$_n$-H;
CH$_3$-O-(CH$_2$-CH$_2$O)$_m$-[CH$_2$-CH(CH$_3$)O]$_n$-H; and $CH_3\text{-}O\text{-}(CH_2\text{-}CH_2O)_n\text{-}[CH_2\text{-}CH(CH_3)O]_m\text{-}H$; in which m has a value of 10–14 and n has a value of 18–22.

15. A method according to claim 14 in which the product separated from the reaction mixture includes organosilicon polyether compounds having the formulas $CH_3\text{-}(OCH_2CH_2)_m\text{-}O\text{-}SiMeR\text{-}O\text{-}(CH_2CH_2O)_m\text{-}CH_3$;

$CH_3\text{-}(OCH_2CH_2)_n\text{-}O\text{-}SiMeR\text{-}O\text{-}(CH_2CH_2O)_n\text{-}CH_3$; and $CH_3\text{-}(OCH_2CH_2)_m\text{-}O\text{-}SiMeR\text{-}O\text{-}(CH_2CH_2O)_n\text{-}CH_3$; in which Me is methyl, m has a value of 10–14, and n has a value of 18–22.

16. A method according to claim 15 in which m is twelve and n is twenty.

17. The product prepared by the method of claim 1.

18. The product prepared by the method of claim 7.

19. The product prepared by the method of claim 12.

20. A method of conditioning skin comprising applying to the skin an effective amount of a mixture of at least three silicone polyethers prepared by a method selected from the group consisting of methods as defined in claims 1, 7, and 12.

* * * * *